(12) United States Patent
Büchmann et al.

(10) Patent No.: US 7,486,388 B2
(45) Date of Patent: Feb. 3, 2009

(54) METHOD AND APPARATUS FOR STANDARDIZATION OF A MEASURING INSTRUMENT

(75) Inventors: Bo Büchmann, Frederiksberg (DK); Mark Westerhaus, State College, PA (US); Sven-Anders Nilsson, Nyhamnsläge (SE); Anders Ebelin, Kågeröd (SE)

(73) Assignee: Foss Tecatur AB, Hoganas (SE)

( * ) Notice: Subject to any disclaimer, the term of this patent is extended or adjusted under 35 U.S.C. 154(b) by 89 days.

(21) Appl. No.: 11/790,754

(22) Filed: Apr. 27, 2007

(65) Prior Publication Data

US 2008/0168822 A1 Jul. 17, 2008

Related U.S. Application Data

(62) Division of application No. 10/283,170, filed on Oct. 30, 2002, now Pat. No. 7,227,623.

(30) Foreign Application Priority Data

Sep. 19, 2002 (SE) .................................. 0202780

(51) Int. Cl.
*G01N 21/00* (2006.01)
*G12B 13/00* (2006.01)
*G01K 1/16* (2006.01)

(52) U.S. Cl. .................. 356/73; 356/72; 356/71; 356/246; 356/128; 250/252.1; 250/339.09; 600/323; 374/131

(58) Field of Classification Search ............. 356/71–73, 356/128–135, 36–41, 445–447, 244, 246, 356/317–319; 250/339.09, 339.12, 252.1, 250/548.1; 600/322, 323, 310, 300, 459, 600/458; 607/5, 60; 373/131, 142; 128/700, 128/710

See application file for complete search history.

(56) References Cited

U.S. PATENT DOCUMENTS 3,741,660 A 6/1973 Abu-Shumays et al.

(Continued)

FOREIGN PATENT DOCUMENTS

| DE | 196 03 000 A1 | 7/1997 |
|---|---|---|
| EP | 0 374 034 | 6/1990 |
| WO | WO96/13709 | 10/1995 |

*Primary Examiner*—Sang Nguyen
(74) *Attorney, Agent, or Firm*—Harness, Dickey & Pierce, P.L.C.

(57) ABSTRACT

A method, a portable device and a measuring instrument for standardization of a satellite measuring instrument to a corresponding master measuring instrument are disclosed. The portable device includes a device for containing a reference material, and an information unit for storing information about the reference material and measurements of the reference material on the master measuring instrument. When placed in a satellite measuring instrument, information from the master instrument stored in the information unit of the portable device is transmitted automatically and wirelessly to the satellite instrument and, together with measurements by the satellite instrument of the reference masterial in the portable device, a standardization model for the satellite instrument and the sample type is obtained.

20 Claims, 4 Drawing Sheets

U.S. PATENT DOCUMENTS

| | | |
|---|---|---|
| 3,776,642 A | 12/1973 | Anson et al. |
| 3,960,497 A | 6/1976 | Acord |
| 4,890,916 A | 1/1990 | Rainer |
| 4,988,211 A | 1/1991 | Barnes et al. |
| 5,343,869 A | 9/1994 | Pross et al. |
| 5,488,571 A | 1/1996 | Jacobs et al. |
| 5,500,639 A | 3/1996 | Walley et al. |
| 5,691,812 A | 11/1997 | Bates et al. |
| 5,724,025 A | 3/1998 | Tavori |
| 5,917,414 A | 6/1999 | Oppelt et al. |
| 5,926,438 A | 7/1999 | Saito |
| 5,931,791 A | 8/1999 | Saltzstein et al. |
| 5,946,083 A | 8/1999 | Melendez et al. |
| 6,073,476 A | 6/2000 | Reents |
| 6,081,326 A | 6/2000 | Rousseau et al. |
| 6,141,584 A | 10/2000 | Rockwell et al. |
| 6,167,258 A | 12/2000 | Schmidt et al. |
| 6,215,403 B1 | 4/2001 | Chan et al. |
| 6,475,153 B1 | 11/2002 | Khair et al. |
| 6,478,748 B1 | 11/2002 | Kuhn et al. |
| 6,486,944 B1 | 11/2002 | Bleyle |
| 6,490,030 B1 | 12/2002 | Gill et al. |
| 6,584,336 B1 | 6/2003 | Ali et al. |
| 6,837,095 B2 | 1/2005 | Sunshine et al. |
| 6,880,968 B1 * | 4/2005 | Haar .......................... 374/131 |
| 6,897,788 B2 * | 5/2005 | Khair et al. ............ 340/870.16 |
| 6,898,451 B2 * | 5/2005 | Wuori ........................ 600/322 |
| 7,268,864 B2 * | 9/2007 | Chiarello et al. ............ 356/128 |
| 2004/0262510 A1 * | 12/2004 | Springsteen et al. ..... 250/252.1 |

\* cited by examiner

METHOD AND APPARATUS FOR STANDARDIZATION OF A MEASURING INSTRUMENT

This application is a divisional application, and claims priority under 35 U.S.C. § 120 to application Ser. No. 10/283,170 filed on Oct. 30, 2002 now U.S. Pat. No. 7,227,623, which claims priority under 35 U.S.C. § 119 to Sweden Patent Application No. 0202780-3 filed on Sep. 19, 2002, in the Sweden Intellectual Property Office. The entire contents of both of these applications are incorporated herein by reference.

TECHNICAL FIELD OF THE INVENTION

The present invention generally relates to a portable device and a method for standardization of a satellite measuring instrument to a corresponding master measuring instrument.

BACKGROUND OF THE INVENTION

Spectral measuring, or analytical instruments, like Near Infrared Reflection (NIR) and Near Infrared Transmission (NIT) instruments, are widely used in e.g. the food industry or in agriculture to analyse the composition and nutritive value of foods and of crops such as forages. For example, the amount of constituents such as crude protein, fat, and carbohydrates may be determined by spectral analysis.

Direct analyses of e.g. a sample of rice on two spectral analysis instruments of the same design will probably produce somewhat different results. The differences may be due to manufacturing variability and instability of the instruments.

In order to obtain comparable results when analyzing the same sample on several spectral analyzers of the same design, the instruments are standardized. Thus, after standardization, the analytical results from each of several "satellite" instruments, i.e. instruments located at different measurement sites, are corrected so that they correspond to the analytical results from a "master" instrument.

In this standardization procedure, a so called "standardization cup" containing a reference material is usually used. This standardization cup is hermetically sealed so that the quality of the reference material is maintained over a long period of time. Firstly, the reference material is analyzed using the master instrument. The result from this analysis, in the form of a "master" spectrum of the reference material, is stored on a disc together with information identifying the reference material and information identifying the master instrument.

Thereafter, this disc and the standardization cup are sent to a user of a satellite instrument. The standardization cup is then put into the satellite instrument and the disc is inserted into a computer connected to the satellite instrument. The reference material is then analysed by the satellite instrument whereby a "satellite" spectrum for the sample is produced. This satellite spectrum is then compared to the master spectrum on the disc by means of a software program on the computer. If the satellite spectrum differs from the master spectrum, which is usually the case, the program produces a standardization model which mathematically transforms the satellite spectrum to correspond to the master spectrum. The standardization model is then stored on the computer and may be used to transform the results of future routine analyses on the satellite instrument for samples of the same type of material as the reference material.

A problem with this known standardization procedure is that there is always a risk that a disc with "standardization" information relating to a specific reference material is lost, or worse, is confused with some other standardization disc for another reference material. The consequences of lost standardization discs are delayed or cancelled standardizations. The consequence of confusion as to the identity of standardization discs is error in predicted values for all routine samples measured on that satellite instrument, at least until the next time the satellite instrument is standardized.

For a standard routine analysis, where the composition of an unknown sample (e.g. grain from a process line) is to be analyzed, an operator puts the sample into a sample cup and the sample cup into the (satellite) instrument. Then the operator enters information about the sample type (grain etc.) on the computer, chooses from a data base on the computer an appropriate standardization model and a prediction model to be applied to the sample and starts the analysis of the sample by the instrument. During the analysis, a spectrum of the sample material is collected, standardized and has a prediction model applied to it in order to translate this standardized spectrum to predictions of chemical composition. It is desirable that routine analysis of samples is more automated, so that mistakes due to "the human factor" may be eliminated and the procedure may be quicker. With the existing system there is always a risk of having erroneous prediction values if the operator chooses the wrong standardization model or prediction model.

SUMMARY OF THE INVENTION

An objective of an embodiment of the present invention is to provide an improved method for standardization of a satellite measuring instrument to a corresponding master measuring instrument.

A particular objective of an embodiment of the invention is to provide increased security of the standardization procedure.

Another objective of an embodiment of the present invention is to provide an improved method for obtaining a standardized result when by routine measuring a sample material by means of a satellite measuring instrument.

Another particular objective of an embodiment of the invention is to facilitate a higher level of automation of both the standardization procedure and the procedure for routine analysis of a sample material.

For achieving at least some of these, and other objectives, a portable device according to an embodiment of the invention, a measuring instrument according to an embodiment of the invention, a method of managing information according to an embodiment of the invention, a method for standardization of a satellite measuring instrument according to an embodiment of the invention, a method for obtaining a standardized result according to an embodiment of the invention, and a cup according to an embodiment of the invention, are provided.

More particularly, according to an embodiment of the invention, a portable device for standardization of a satellite measuring instrument to a corresponding master measuring instrument comprises a means for containing a reference material, and an information unit for storing information about the reference material and about measurements of the reference material on the master measuring instrument. By physically binding the standardization information together with the reference material in one "portable device", the risk of choosing the wrong standardization information, or losing the information, is as good as eliminated. Thus, the portable device should here be seen as a single unit device. The portable device may comprise a standardization cup as mentioned above, with an information unit in the form of a chip attached to it.

In one embodiment of an embodiment of the invention, the information further is about said master measuring instrument. Thereby, the master measuring instrument may be identified by means of the information, which e.g. could comprise serial number, model number etc. of the master measuring instrument.

In another embodiment of the invention, said information unit is physically attached to said means for containing said reference material. This could be the case if the portable device, as suggested above, comprises a standardization cup with a chip attached to it.

In another embodiment, said information unit comprises a storage means for storing said information. Such a storage means may be in the form of an Electrical Eraseable Programmable Read Only Memory (EEPROM), or some other type of appropriate memory circuit. Since digital memories can be made very small today and still have large storing capacity, a memory may preferably be comprised in the information unit.

According to another embodiment of the invention, said information unit further comprises means for transmitting said information to said satellite measuring instrument. By means of such arranged transmitting means being part of the information unit, the information may easily be loaded into the satellite measuring instrument for enabling the standardization procedure.

According to another embodiment, said means for transmitting said information is arranged for wireless data transfer. This is advantageous since no "plugging in" is then needed in order to transmit the information to the satellite measuring instrument.

According to yet another embodiment, said means for transmitting said information comprises a radio frequency identifier. A radio frequency identifier of today allows wireless non-contact reading and is relatively cheap, may have a robust construction and may include read and write electronic storage technology.

In another embodiment of the invention, said information about the reference material comprises identification of said reference material. Thus, the reference material can be identified and the identification information may be stored together with the standardization model to be produced for that specific type of material.

In another embodiment, said information about the reference material further comprises an expiry date of said reference material. Thereby, the risk that measurements are made on an old, degraded reference material may be eliminated.

According to another embodiment of the invention, said information about measurements of the reference material on the master instrument comprises a reference spectrum. A reference spectrum may be used to standardize a satellite instrument in the form of a spectral analysis instrument.

According to one embodiment, said reference spectrum is within the entire electro-magnetic wavelength range.

According to another embodiment, said reference spectrum is within the visible and infrared wavelength interval. Common spectral analysis instruments like e.g. NIR and NIT instruments work within this wavelength interval.

In one embodiment of the invention, said reference spectrum is measured by means of said master measuring instrument being a visible and near infrared reflection measuring instrument.

In another embodiment of the invention, said reference spectrum is measured by means of said master measuring instrument being a visible and near infrared transmission measuring instrument.

In one embodiment, said means for containing said reference material is hermetically sealable. Thereby, the quality of the reference material may be maintained over a long period of time.

In another embodiment, said means for containing said reference material allows visible and near infrared reflection measurements of said reference material being contained in said means for containing said reference material. This may be achieved by means of a window to a chamber of said means for containing said reference material.

In yet another embodiment, said means for containing said reference material allows visible and near infrared transmission measurements of said reference material being contained in said means for containing said reference material. This may be achieved by means of two windows to a chamber of said means for containing said reference material.

According to the invention, a measuring instrument for routine measurement of a sample material comprises a receiving means for receiving a sample container containing said sample material, a means for measuring said sample material when said sample container is located in said receiving means, and a means for reading information from an information unit of a portable device containing a reference material when said portable device is located in said receiving means. By providing the measuring instrument with a means for reading information from an information unit of a portable device according to above, standardization information regarding the reference material may quickly, simply and safely be transferred to the measuring instrument and used to produced a standardization model for such material.

According to one embodiment of the invention, said means for reading information is arranged to read said information wirelessly. This is advantageous because the information unit does not need to be physically connected to the measuring instrument, whereby the reading of the information gets even more quick and simple.

According to another embodiment of the invention, said information is about said reference material and measurements of said reference material on a master measuring instrument corresponding to said measuring instrument. Such information allows standardization of the measuring instrument to be made.

According to another embodiment, said information further is about said master measuring instrument. Thereby, e.g. the specific type of the master measuring instrument may be identified.

According to yet another embodiment, said means for measuring said sample material is arranged to automatically start measuring on said reference material when said portable device is located in said receiving means. This makes both routine analyses and the procedure of standardizing measuring instruments faster and easier.

In another embodiment of the invention, said means for reading information from said information unit of said portable device is arranged to automatically start reading said information when said portable device is located in said receiving means. This too may make both routine analyses and the procedure of standardizing measuring instruments faster and easier.

In another embodiment, said means for reading said information comprises a radio frequency identification reader. As mentioned above, Radio Frequency Identification (RFID) technology allows wireless reading while being relatively cheap and robust.

In another embodiment, said measuring instrument is a visible and near infrared reflection measuring instrument.

In yet another embodiment, said measuring instrument is a visible and near infrared transmission measuring instrument.

According to one aspect of the present invention, a method of managing information, obtained by means of a master measuring instrument, regarding a reference material for standardization of a satellite measuring instrument comprises storing said information in an information unit which is a part of a portable device which also comprises a means for containing said reference material, transporting said portable device from said master measuring instrument to said satellite measuring instrument, and transmitting said information from said information unit of said portable device to said satellite measuring instrument.

This inventive method of managing information regarding a reference material increases the security of the information management, so that the risk of choosing the wrong standardization information, or losing the information, is as good as eliminated.

According to another aspect of the invention, a method for standardization of a satellite measuring instrument to a corresponding master measuring instrument comprises measuring, by means of said satellite measuring instrument, a reference material being contained in a means for containing said reference material of a portable device, reading, by means of said satellite measuring instrument, information about a corresponding measurement, obtained by means of said master measuring instrument, from an information unit which is a part of said portable device, and producing and storing a standardization model describing a difference between the result of said action of measuring said reference material and said corresponding measurement obtained by means of said master measuring instrument.

As mentioned above, this standardization model allows the satellite measuring result, for example in the form of a spectrum, to be mathematically transformed to correspond to the master measurement. The standardization model may be seen as a way of converting the satellite measuring result into a standardized measuring result.

According to the invention, by reading the information from an information unit which is a part of said portable device, the standardization procedure can be made faster and more secure.

According to one embodiment of this inventive method, said information further is about said reference material and said master measuring instrument.

According to another embodiment, said method is performed by the help of an external computer. Thereby, less "intelligent" satellite measuring instruments may be standardized.

According to yet another embodiment, said action of producing and storing said standardization model is performed by means of said external computer.

In one embodiment of said inventive method, said method is performed automatically when said portable device is located in a receiving means of said satellite measuring instrument. This makes the procedure of standardizing the satellite measuring instrument faster and easier, requiring less measures to be taken by a user.

In another embodiment, said satellite measuring instrument is a visible and near infrared reflection measuring instrument.

In yet another embodiment, said satellite measuring instrument is a visible and near infrared transmission measuring instrument.

According to yet another aspect of the present invention, a method for obtaining a standardized result when by routine measuring a sample material by means of a satellite measuring instrument, such that the difference between said result and the result that would have been obtained if the sample material had been measured by means of a corresponding master measuring instrument is minimized, comprises measuring, by means of said satellite measuring instrument, said sample material being contained in a means for containing said sample material of a portable device, reading, by means of said satellite measuring instrument, information from an information unit, which is a part of said portable device, wherein said information comprises information of the identity of the type of said sample material, selecting the correct standardization model according to said information of the identity of the type of said sample material from amongst at least a few standardization models stored in at least one of the satellite instrument and an external computer connected to the satellite measuring instrument, and applying said standardization model to the spectrum of said sample material so that a standardized spectrum of said sample material is produced that is essentially identical to the spectrum that would have been obtained by means of said master measuring instrument.

According to this inventive method, the inventive portable device may be used also for obtaining a standardized result when by routine measuring a sample material by means of a satellite measuring instrument. The inventive method makes standardized routine measurements faster, easier and more secure.

In one embodiment of this inventive method, said reading of said information is made wirelessly.

In another embodiment, said information of the identity of the type of said sample material further is used to select the correct prediction model from amongst at least a few prediction models stored in at least one of said satellite measuring instrument and said external computer.

As mentioned above, a prediction model is used to translate, or mathematically convert, the spectral information into analytical information, i.e. information in the form of chemical quantities. Hence, the prediction model may be seen as a way of converting the spectral information into analytical information.

In another embodiment, said method further comprises applying said prediction model to said standardized spectrum of said sample material in order to obtain the desired analytical result for said sample material that is essentially identical to the result that would have been obtained by means of said master measuring instrument.

According to another embodiment, said method is performed automatically when said portable device is located in a receiving means of said satellite measuring instrument.

According to yet another embodiment, said satellite measuring instrument is a visible and near infrared reflection measuring instrument.

According to yet another embodiment, said satellite measuring instrument is a visible and near infrared transmission measuring instrument.

According to the invention, a cup for receiving and containing a material to analyse supports a chip for storing information about said material and for wirelessly transmitting said information to a measurement instrument for measuring said material.

BRIEF DESCRIPTION OF THE DRAWINGS

The present invention will now be described in more detail with reference to the accompanying drawings, in which.

DETAILED DESCRIPTION OF PREFERRED EMBODIMENTS

Figure 1:
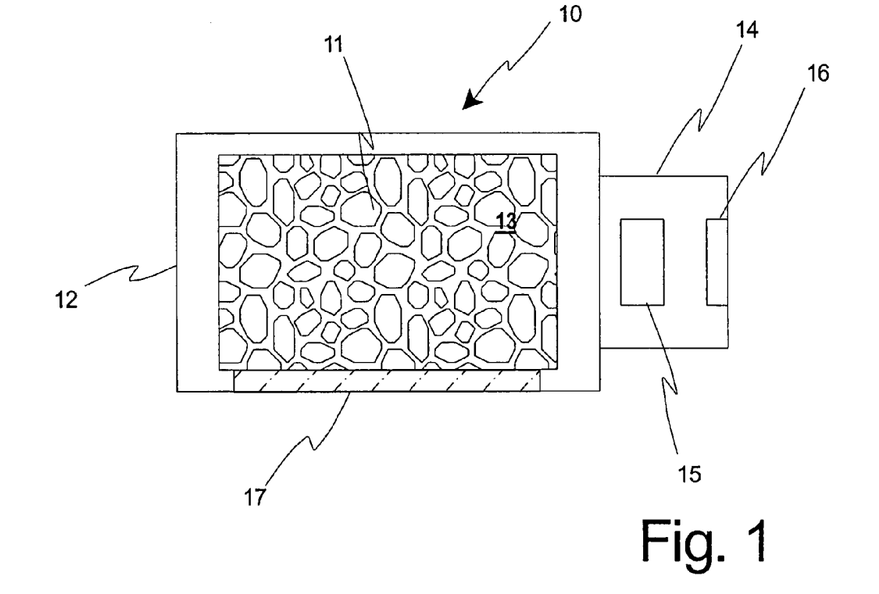
FIG. 1 is a simplified schematic view of one embodiment of a portable device according to the invention.

FIG. 1 shows one embodiment of a portable device 10 according to the invention.

The portable device 10 comprises a means for containing a reference or sample material 11, here in the form of a container 12 defining a chamber 13 for containing the material 11. The container 12 may be arranged to allow spectral measurements, such as e.g. visible and near infrared reflection and/or transmission measurements, of the material 11 while the material 11 is contained in the chamber 13. In FIG. 1 is shown an analysis window 17 of the portable device 10 through which visible and near infrared reflection measurements can be made. In order to allow also visible and near infrared transmission measurements, the portable device 10 may be provided with another analysis window (not shown) on the opposite side of the chamber 13.

The inventive portable device 10 further comprises an information unit 14, which is supported by the container 12, and which includes a storage means, here in the form of a memory 15, for storing information regarding the material. The memory 15 may be an Electrical Eraseable Programmable Read Only Memory (EEPROM), or some other type of appropriate memory circuit.

The information unit 14 also includes a means for transmitting the information to a measuring instrument or to an external computer connected to a measuring instrument, which means for transmitting here is in the form of a transmitter 16 being arranged for wireless data transfer.

Figure 2:
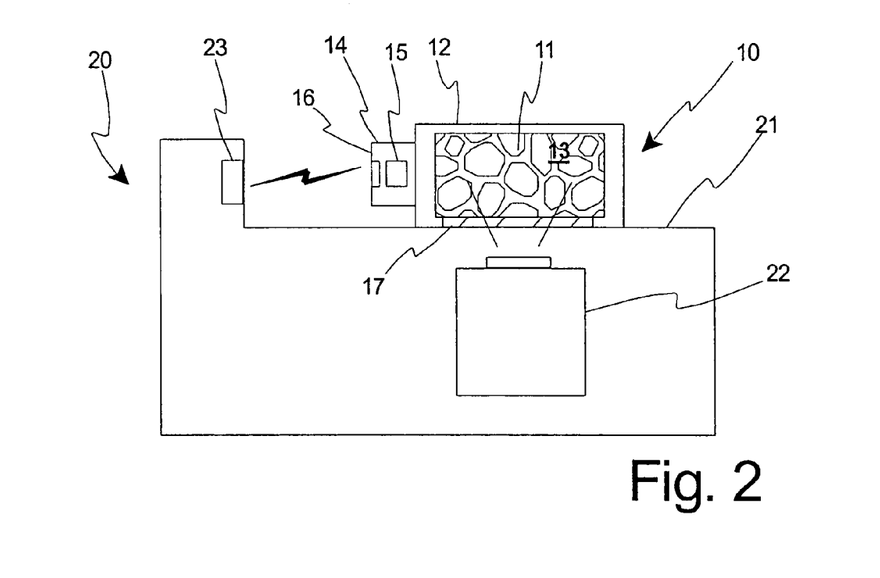
FIG. 2 is a simplified schematic view illustrating the interaction between one embodiment of a measuring instrument according to the invention and a portable device as shown in FIG. 1.

FIG. 2 shows one embodiment of a measuring instrument according to the invention, here in the form of a spectral analysis instrument 20, e.g. a visible and near infrared reflection and/or transmission measuring instrument, and a portable device 10 as shown in FIG. 1. The portable device 10 in FIG. 2 is located upon a receiving means 21 of the spectral analysis instrument 20, where a material 11 inside the chamber 13 of the container 12 may be presented for a means for measuring the material 11, here in the form of a detector 22 of the spectral analysis instrument 20.

The inventive measuring instrument further comprises a means, here a reader (or receiver) 23, for wirelessly reading the information from the information unit 14 of the portable device 10.

The communication between the transmitter 16 of the information unit 14 and the reader 23 may be wireless, whereby no physical connection would be needed in order to transmit the information stored in the memory 15 of the information unit 14 to the spectral analysis instrument 20. The wireless communication may be implemented according to any common protocol for wireless data transfer, for example IEEE 802.11 or Bluetooth, or, preferably, in a more simple way according to any standard for Radio Frequency Identification (RFID).

The measuring instrument may be arranged so that it automatically starts measuring the material 11 when the portable device 10 is placed upon the receiving means 21. The measuring instrument may further be arranged to automatically start reading the information from the information unit 14 when the portable device 10 is placed upon the receiving means 21.

Figure 3:
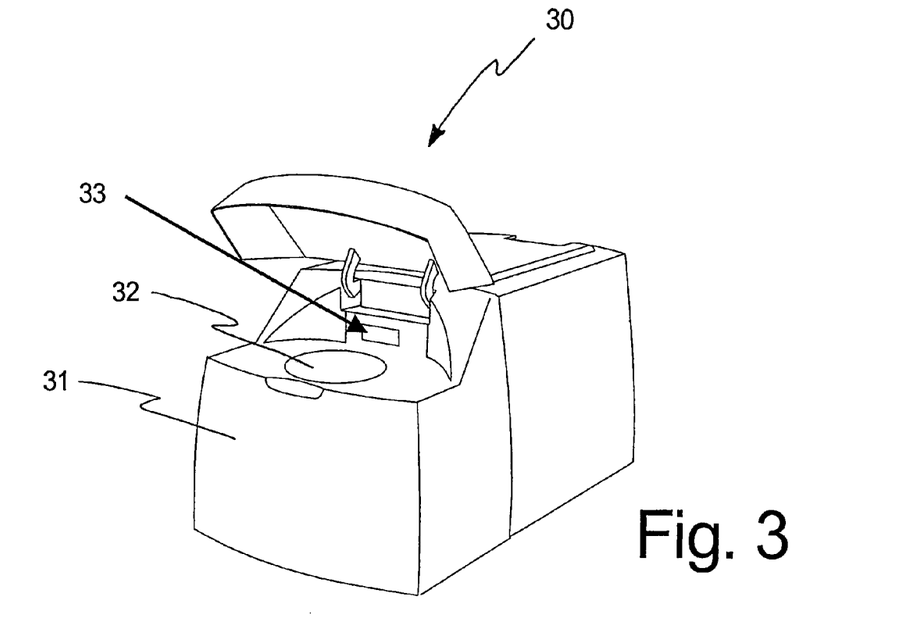
FIG. 3 is a more detailed schematic perspective view of another embodiment of a measuring instrument according to the invention.

FIG. 3 shows another, and more detailed, embodiment of a measuring instrument according to the invention. What is shown is the casing 31 of a spectral analysis instrument 30, including a receiving means in the form of a plate 32 for receiving and supporting a portable device with a content to be analyzed. The spectral analysis instrument 30 shown also includes an RFID reader with an interface 33 for wirelessly reading information from an information unit of an inventive portable device.

Figure 4:
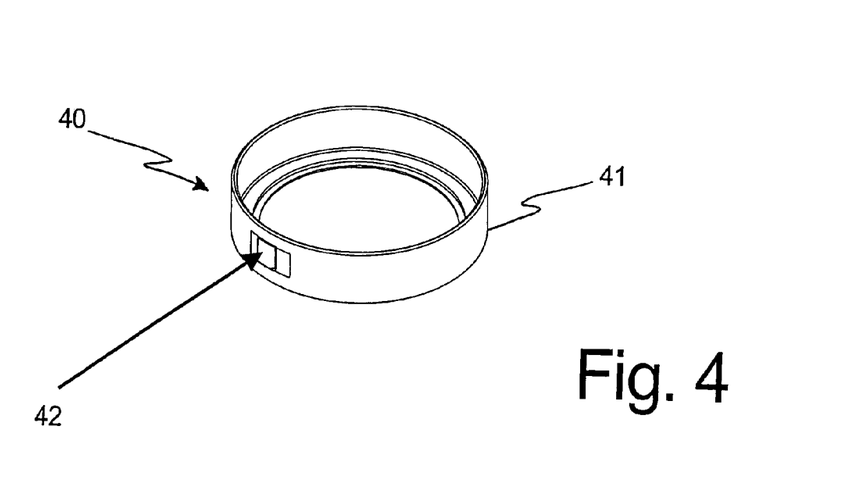
FIG. 4 is a schematic perspective view of another embodiment of a portable device according to the invention.

FIG. 4 shows another, and more detailed, embodiment of a portable device 40 according to the invention. Here, the portable device 40 is in the form of a cup 41 into which a reference or sample material may be put. If a material is to be contained in the cup 41 for a long time, which is usually the case when the material is a reference material, the cup 41 may be hermetically sealed by means of a lid (not shown). Onto the cylindric wall of the cup 41, an RFID tag (or chip) 42 is attached. The RFID tag 42 contains a memory for storing of information regarding the material in the cup 41.

In the case where the portable device is used for standardization, the information stored in the memory of the information unit (14 in FIGS. 1 and 2 or 42 in FIG. 4) is about the reference material, a master measuring instrument, and measurements of the reference material on the master measuring instrument. More particularly, the information comprises identification of both the reference material and the master measuring instrument, plus data about the reference material collected by the master measuring instrument during measurement of the reference material by the master measuring instrument.

The data about the reference material may be in the form of a reference spectrum collected by the master measuring instrument. The reference spectrum may be within the entire electromagnetic wavelength range, or preferably within the visible and infrared wavelength interval.

The information stored in the memory of the information unit may also comprise an expiry date of the reference material, and information about the temperature of the reference material during the measurement of it by the master measuring instrument.

Now, referring to the flow chart of FIG. 5, a method for standardization of a satellite measuring instrument to a corresponding master measuring instrument will be described.

Figure 5:
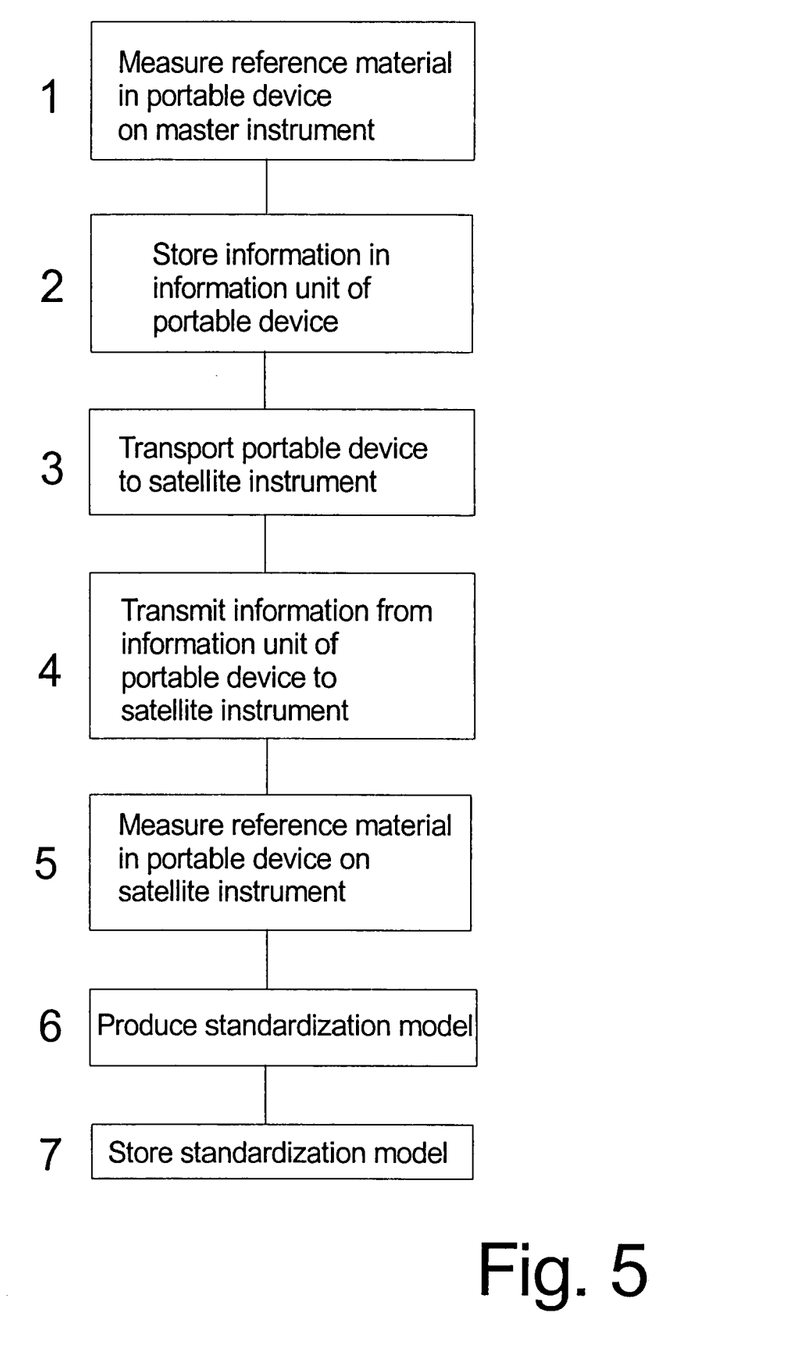
FIG. 5 is a flow chart illustrating the steps of an embodiment of a method according to the invention for standardization of a satellite measuring instrument to a corresponding master measuring instrument.

In step 1 of FIG. 5, a reference material, being contained in a portable device according to the invention, is measured on a master measuring instrument.

In step 2, information identifying the master measuring instrument, the reference material and the type of portable device is transmitted wirelessly from the master instrument, or from an external computer connected to the master instrument, to the information unit of the portable device and stored in the memory comprised in the information unit. Further, the transmitted information includes the result, in the form of reference spectral data, of the measurement of the reference material on the master instrument. In this step, fast and easy storing of the information together with the reference material is provided.

In step 3, the portable device is transported from the master instrument to a user of a satellite instrument and put onto the satellite measuring instrument which is to be standardized. In this step, increased security of the transport and management of the information, which is to be used together with the reference material for standardization of the satellite measuring instrument, is provided. Since this standardization information is physically bound together with the reference material in the portable device, the risk of choosing the wrong standardization information, or losing the information, is as good as eliminated.

In step 4, the information stored in the information unit of the portable device is transmitted wirelessly to the satellite instrument. This step may be performed automatically when the portable device is placed on the satellite instrument. By transmitting the information wirelessly and automatically to the satellite instrument, the procedure gets quick and simple.

In step 5, the reference material contained in the portable device is measured by the satellite instrument. This step may also be performed automatically when the portable device is placed on the satellite instrument, and may thus be performed without delay.

In step 6, a standardization model is produced by the satellite instrument, or by an external computer connected to the satellite instrument, after comparison of the result from step 5 and the result, transmitted from the information unit of the portable device, from step 1. The standardization model describes the difference between the result obtained by measuring the reference material on the satellite instrument and the corresponding result obtained by measuring the reference material on the master instrument.

In step 7, the standardization model that is produced, is stored in a data base either in the satellite instrument or in an external computer connected to the satellite instrument. The standardization model may be one amongst several stored in the satellite instrument or the external computer connected to the instrument.

As used herein, "standardization" means to obtain, by measuring a reference material on a satellite instrument, a standardization model, which may be used with routine measurements of samples of the same type in order to obtain a standardized spectrum. This means that the standardized spectrum corresponds to the spectrum which would have been obtained on the master measuring instrument. A standardization model is unique to the sample type and the master/satellite instrument pair.

Figure 6:
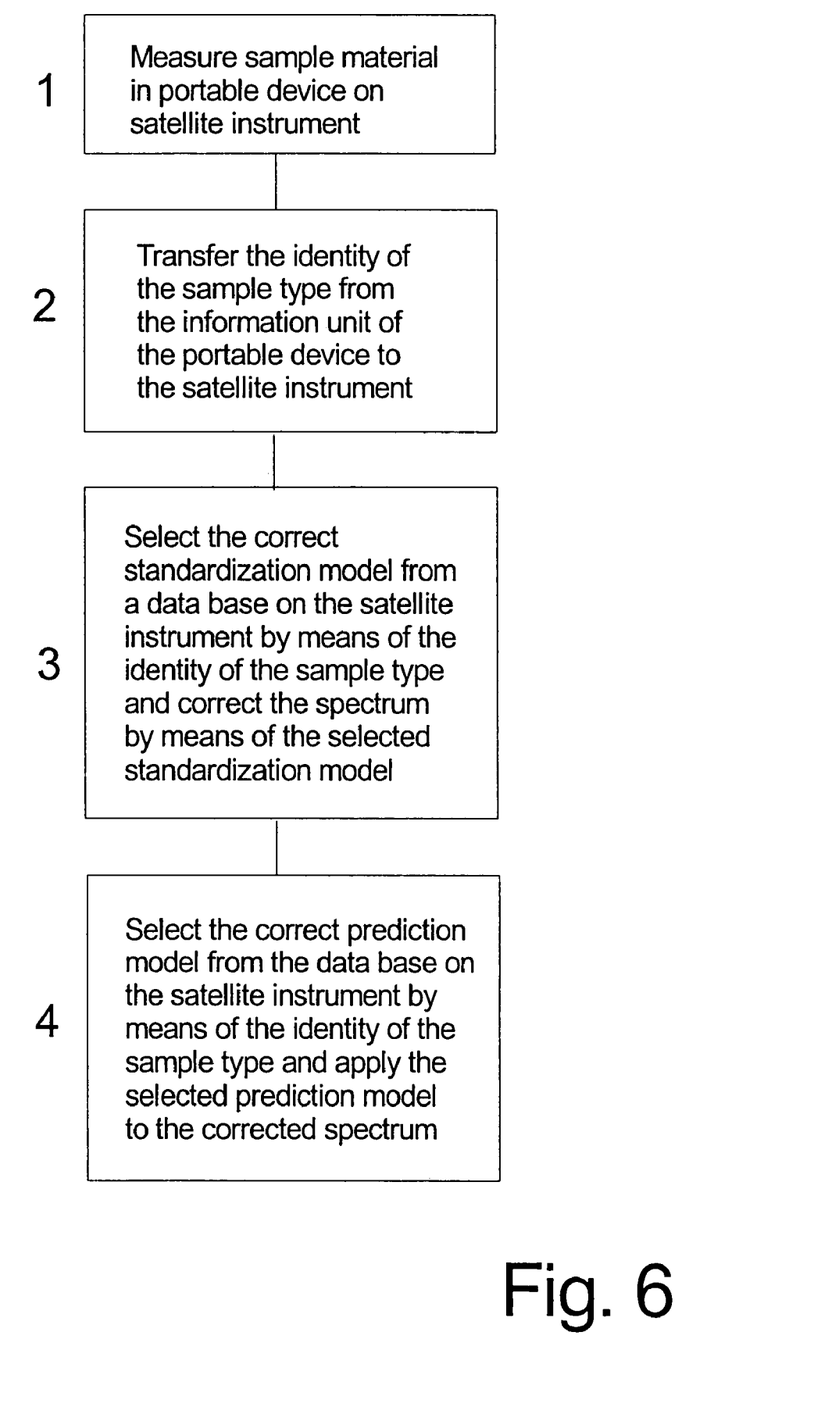
FIG. 6 is a flow chart illustrating the steps of an embodiment of a method according to the invention for obtaining a standardized result when routinely measuring a sample material by means of a satellite measuring instrument.

Referring to FIG. 6, a portable device according to the invention may also be used for routine analysis of a sample material. In this case, the information stored in the memory of the information unit (14 in FIGS. 1 and 2 or 42 in FIG. 4) may include information of the type of material in the portable device. The information of the sample type is transferred to the satellite instrument or the external computer connected to the instrument, and in turn used to identify the correct standardization model to be applied to the spectrum of the routine sample.

The information of the sample type may also be used to identify the correct prediction model, stored amongst several on the instrument or the external computer connected to the instrument, to be used for converting the standardized spectrum of the routine sample into an analytical result.

Referring to the flow chart in FIG. 6, this method for obtaining a standardized result, when routinely measuring a sample material by means of a satellite measuring instrument, will be described stepwise.

As will be seen from the following described steps, corresponding advantages with increased security and decreased delays, that were mentioned in connection with the method for standardization according to FIG. 5, counts for the routine analysis according to FIG. 6.

In step 1 of FIG. 6, a sample material, contained in a portable device according to the invention, is measured on a satellite instrument. The measurement may start automatically when the portable device is placed on the satellite instrument.

In step 2, the identity of the sample type is transferred wirelessly from the memory of the information unit of the portable device to the satellite instrument or the external computer connected to the satellite instrument. Additional information related to the sample itself or the sample cup may also be transferred.

In step 3, the correct standardization model is selected, from a data base on the instrument or the external computer connected to the instrument, by means of the identity of the sample type and applied to the spectrum of the routine sample from step 1. Thereby, the spectrum is corrected so that it is essentially identical to the spectrum that would have been obtained by means of the master instrument.

In step 4, the identity of the sample type is used to select the correct prediction model, from the data base on the instrument or the external computer connected to the instrument. The selected prediction model is applied to the corrected spectrum in order to obtain the desired analytical result for the sample material that is essentially identical to the result that would have been obtained by means of the master instrument.

A portable device according to the invention may either be used for standardization by means of a reference material contained in the portable device or for routine analysis of a sample material contained in the portable device.

Regardless of whether the portable device is used for standardization or for routine analysis, the information stored in the information unit of the portable device may also include identification of the type of the portable device, for example cup size, reflection/transmission characteristics etc.

Regardless of whether the portable device is used for standardization or for routine analysis, the information unit of the portable device may also comprise a temperature sensor for sensing the temperature in the vicinity of the reference or sample material during measurement. The information unit may then be arranged to transmit this information to the measuring instrument, or to an external computer connected to the measuring instrument.

Even though this description of the present invention only has concerned its applicability to spectal analysis of material characteristics, the invention may also be applicable to other types of measurements of mechanical, chemical and optical characteristics. The inventive portable device and measuring instrument may then be modified and adapted for the specific type of measurement. Also the specific information stored in the information unit of the inventive portable device may be adapted for other types of measurements. Examples of such other types of measurements are chromatography, isotope analysis, image analysis and other types of electromagnetic waves analyses.

It is to be understood that modifications of the above-described portable devices, measuring instruments and methods can be made by people skilled in the art without departing from the spirit and scope of the invention.

The invention claimed is:

1. A measuring instrument for routine measurement of a sample material, comprising
    a receiving means for receiving a sample container containing said sample material;
    a means for measuring said sample material when said sample container is located in said receiving means, and for measuring a reference material being contained in a portable device when said portable device is located in said receiving means;
    a means for reading information from an information unit of said portable device containing said reference material when said portable device is located in said receiving means, wherein said information is about said reference material and corresponding measurements of said reference material on a master measuring instrument; and
    a means for processing said information to obtain a standardization model.

2. A measuring instrument according to claim 1, wherein said standardization model describes the difference between the result of measuring said reference material and said corresponding measurement obtained by means of said master measuring instrument.

3. A measuring instrument according to claim 1, wherein said means for processing is also adapted to select, depending on the type of the sample material, a correct standardization model from a plurality of stored standardization models.

4. A measuring instrument according to claim 1, wherein said means for processing comprises an external computer.

5. A measuring instrument according to claim 1, wherein said means for reading information is arranged to read said information wirelessly.

6. A measuring instrument according to claim 1, wherein said information further is about said master measuring instrument.

7. A measuring instrument according to claim 1, wherein said means for measuring said sample material is arranged to automatically start measuring on said reference material when said portable device is located in said receiving means.

8. A measuring instrument according to claim 1, wherein said means for reading information from said information unit of said portable device is arranged to automatically start reading said information when said portable device is located in said receiving means.

9. A measuring instrument according to claim 1, wherein said means for reading said information comprises a radio frequency identification reader.

10. A measuring instrument according to claim 1, wherein said measuring instrument is a visible and near infrared reflection measuring instrument.

11. A measuring instrument according to claim 1, wherein said measuring instrument is a visible and near infrared transmission measuring instrument.

12. A measuring instrument for routine measurement of a sample material, comprising
    a container configured to receive a sample container containing said sample material;
    a detector configured to measure said sample material when said sample container is located in said container, and for measuring a reference material being contained in a portable device when said portable device is located in said container;
    a reader configured to read information from an information unit of said portable device containing said reference material when said portable device is located in said container, wherein said information is about said reference material and corresponding measurements of said reference material on a master measuring instrument; and
    a processor configured to process said information to obtain a standardization model.

13. A measuring instrument according to claim 12, wherein said
    standardization model describes the difference between the result of measuring said reference material and said corresponding measurement obtained by means of said master measuring instrument.

14. A measuring instrument according to claim 12, wherein said processor is also configured to select, depending on the type of the sample material, a correct standardization model from a plurality of stored standardization models.

15. A measuring instrument according to claim 12, wherein said processor comprises an external computer.

16. A measuring instrument according to claim 12, wherein said reader is arranged to read said information wirelessly.

17. A measuring instrument according to claim 12, wherein said information further is about said master measuring instrument.

18. A measuring instrument according to claim 12, wherein said detector is arranged to automatically start measuring on said reference material when said portable device is located in said container.

19. A measuring instrument according to claim 12, wherein said reader is arranged to automatically start reading said information when said portable device is located in said container.

20. A measuring instrument according to claim 12, wherein said reader includes a radio frequency identification reader.

* * * * *